(12) United States Patent
Radon

(10) Patent No.: US 12,130,236 B2
(45) Date of Patent: Oct. 29, 2024

(54) METHOD FOR CREATING A DATABASE FOR DETERMINING A LIGHT TRANSMISSION AGGREGOMETRY REFERENCE VALUE, AND METHOD AND DEVICE FOR CARRYING OUT A LIGHT TRANSMISSION AGGREGOMETRY MEASUREMENT

(71) Applicant: Kommanditgesellschaft Behnk Elektronik GmbH & Co., Norderstedt (DE)

(72) Inventor: Christian Radon, Hamburg (DE)

(73) Assignee: Kommanditgesellschaft Behnk Elektronik GmbH & Co., Norderstedt (DE)

( * ) Notice: Subject to any disclaimer, the term of this patent is extended or adjusted under 35 U.S.C. 154(b) by 0 days.

(21) Appl. No.: 18/294,454

(22) PCT Filed: Jul. 22, 2022

(86) PCT No.: PCT/EP2022/070619
§ 371 (c)(1),
(2) Date: Feb. 1, 2024

(87) PCT Pub. No.: WO2023/016778
PCT Pub. Date: Feb. 16, 2023

(65) Prior Publication Data
US 2024/0272085 A1    Aug. 15, 2024

(30) Foreign Application Priority Data
Aug. 10, 2021    (EP) .................................... 21190636

(51) Int. Cl.
*G01N 21/82*    (2006.01)
*G01N 21/31*    (2006.01)
(Continued)

(52) U.S. Cl.
CPC ........... *G01N 21/82* (2013.01); *G01N 21/314* (2013.01); *G01N 33/86* (2013.01); *G16B 50/30* (2019.02); *G01N 2021/825* (2013.01)

(58) Field of Classification Search
CPC ...... G01N 21/272; G01N 21/31; G01N 21/82; G01N 33/491; G01N 33/86; G01N 2021/825; G01N 21/314
(Continued)

(56) References Cited

U.S. PATENT DOCUMENTS 3,989,382 A * 11/1976 Kent .................. G01N 33/4905
435/13
5,331,958 A * 7/1994 Oppenheimer ...... G01N 21/532
600/326
(Continued)

FOREIGN PATENT DOCUMENTS

EP    1890142 A2    2/2008
EP    3229012 B1    4/2020
(Continued)

OTHER PUBLICATIONS

Sakayori Tasuku et al, "Evaluation of the Newly Developed Adenosine Diphosphate-Induced Platelet Aggregation Level System in Aggregometer on Automated Coagulation Analyzer", DE vol. 65, No. Dec. 2019, DOI: 10.7754/Clin.Lab.2019.190353, ISSN:1433-6510, Dec. 2019 (Dec. 2019), Clinical Laboratory, Retrieved from the Internet: URL:http://dx.doi.org/10.7754/Clin.Lab.2019.190353, XP055871304, DOI: 10.7754/Clin.Lab.2019.190353, ISSN:1433-6510, cited in the application, abstract, section "Materials and Methods" on pages.
(Continued)

*Primary Examiner* — Arlen Soderquist
(74) *Attorney, Agent, or Firm* — Alix, Yale & Ristas, LLP

(57) ABSTRACT

What is disclosed is a method for creating a database for determining a virtual reference value for a light transmission
(Continued)

aggregometry measurement, comprising the following steps:
a. providing platelet-rich plasma "PRP" (17) of a reference blood sample;
b. performing a light transmission measurement with a first light wavelength and a second light wavelength (14), different from the first, on the PRP (17) of the reference blood sample;
c. providing platelet-poor plasma "PPP" of the reference blood sample;
d. performing a light transmission measurement on the PPP in order to determine a PPP reference value;
e. assigning the measurement result of step d to the measurement results of step b in a database;
f. repeating steps a to e for a plurality of reference blood samples.

The database obtained using this method makes it possible to determine a virtual reference value that is an excellent estimate of the PPP reference value. Once the database has been created, it is possible to determine virtual reference values of blood samples to be examined and perform LTA measurements using the virtual reference values, without the need to obtain PPP from the blood samples to be examined.

14 Claims, 4 Drawing Sheets

(51) Int. Cl.
  *G01N 33/86* (2006.01)
  *G16B 50/30* (2019.01)
(58) Field of Classification Search
  USPC ........................................ 422/73; 436/63, 69
  See application file for complete search history.

(56) References Cited

U.S. PATENT DOCUMENTS

| | | | | |
|---|---|---|---|---|
| 2002/0176068 | A1* | 11/2002 | Fodgaard | G01N 21/05 356/39 |
| 2006/0279725 | A1* | 12/2006 | Coville | G01N 21/59 356/442 |
| 2012/0232803 | A1* | 9/2012 | Viola | G01N 29/028 422/50 |
| 2014/0087472 | A1* | 3/2014 | Kurono | G01N 35/00613 422/67 |
| 2015/0050677 | A1* | 2/2015 | Rade | G01N 33/86 435/13 |
| 2017/0248576 | A1 | 8/2017 | Nishimura et al. | |
| 2019/0276872 | A1* | 9/2019 | Lichte | G01N 33/728 |

FOREIGN PATENT DOCUMENTS

| | | |
|---|---|---|
| JP | 2001159601 A | 6/2001 |
| JP | 200846031 A | 2/2008 |
| JP | 201715501 A | 1/2017 |
| JP | 2017156105 A | 9/2017 |

OTHER PUBLICATIONS

Ling Li-Qin et al, "Evaluation of an automated light transmission aggregometry", GB vol. 28, No. 7, DOI: 10.1080/09537104.2016. 1265923, ISSN:0953-7104, Feb. 2, 2017 (Feb. 2, 2017), p. 712-719, Platelets (London), Retrieved from the Internet: URL:https://www.tandfonline.com/doi/pdf/10.1080/09537104.2016.1265923, XP055871233, DOI: 10.1080/09537104.2016.1265923, ISSN:0953-7104 , cited in the application, abstract, figures 3-8.

Le Blanc Jessica et al, "Advances in Platelet Function Testing-Light Transmission Aggregometry and Beyond", Journal of Clinical Medicine, vol. 9, No. 8, Aug. 13, 2020 (Aug. 13, 2020), p. 2636, XP055871250, DOI: 10.3390/jcm9082636, cited in the application, abstract, p. 5, table 2, 18 pgs.

Mukaide Kae, "Overview of the Automated Coagulation Analyzer CS5100", 2013, Retrieved from the Internet: URL:https://www.sysmex.co.jp/en/products_solutions/library/journal/vol23_no1/vol23_1_02.pdf, XP055871951, [retrieved on Dec. 13, 2021], cited in the application, figures 2, 10, 10pgs.

Streif Werner et al., "Diagnosis of platelet dysfunction—thrombocytopathies", 1 Guideline thrombocytopathies: version 2.1 (AWMF register No. 086-003, update Feb. 2018), Society for Thrombosis and Hemostasis Research (GTH e.V.), 50 pgs.

PCT International Search Report and Written Opinion for International Application No. PCT/EP2022/070619 filed on Jul. 22, 2022, Date of Mailing: Oct. 4, 2022, 24 pgs.

* cited by examiner

METHOD FOR CREATING A DATABASE FOR DETERMINING A LIGHT TRANSMISSION AGGREGOMETRY REFERENCE VALUE, AND METHOD AND DEVICE FOR CARRYING OUT A LIGHT TRANSMISSION AGGREGOMETRY MEASUREMENT

BACKGROUND

The invention relates to a method for creating a database that is able to be used to determine a virtual reference value for a light transmission aggregometry measurement. The invention furthermore relates to a method for determining a virtual reference value for performing a light transmission aggregometry measurement on the platelet-rich plasma of a blood sample to be examined using the created database and performing a light transmission aggregometry measurement using the virtual reference value.

Light transmission aggregometry (LTA) is one of the most commonly used methods for assessing the functionality of platelets. To perform an LTA measurement, what is known as platelet-rich plasma (PRP) is obtained from a blood sample provided by a subject through centrifugation. Due to their disk-like shape with a diameter of between 1.5 µm and 3 µm, light scattering takes place on the platelets, which gives the PRP the appearance of a cloudy fluid. After the addition of an activator to the PRP sample, the platelets cross-link and form aggregates, as a result of which the light transmission of the PRP sample (at least provided that this originates from healthy subjects) increases and the transmittance approaches a maximum over time. As part of an LTA measurement, this increase in transmittance (or decrease in absorbance) is measured over time under standardized conditions by directing a light beam at the PRP sample and measuring the intensity of the light beam emerging from the sample. The document "SAKAYORI TASKUKU ET AL: "Evaluation of the Newly Developed Adenosine Diphosphate induced Platelet Aggregation Level System in Aggregometer on Automated Coagulation Analyzer", CLINICAL LABORATORY, vol. 65, no. 12/2019, Dec. 1, 2019 (2019-12-01), XP 055871304" discloses an LTA method in which what is known as an "ADP-induced platelet aggregation level" (APAL) is used to evaluate the LTA measurement. "LING LI-QIN ET AL: "Evaluation of an automated light transmission aggregometry", PLATELETS (LONDON), vol. 28, no. 7, Feb. 2, 2017 (2017-02-02), pages 712-719, XP 055871233" presents a study on the performance of a coagulation analyzer. The document "LE BLANC JESSICA ET AL: "Advances in Platelet Function Tenting-Light Transmission Aggregometry and Beyond", JOURNAL OF CLINICAL MEDICINE, vol. 9, no. 8, Aug. 13, 2020 (2020-08-13), page 2636, XP 055871250" gives an overview of recent developments in the field of LTA measurement methods. US 2017/248576 A1 discloses an LTA analyzer that has three light sources for emitting three different light wavelengths, wherein the different wavelengths are used for different measuring tasks. The document "Mukaide Kae: "Overview of the Automated Coagulation Analyzer CS5100', Sysmex Journal International, 2013, XP 055871951" provides a product overview of the "CS-5100" automated coagulation analyzer.

In order to be able to interpret the change in light transmission, it is necessary in the prior art, in addition to the PRP sample, to provide a sample of platelet-poor plasma (hereinafter referred to as "PPP") of the same subject. This PPP sample is likewise used to ascertain the transmittance, which is used as a reference value for the LTA measurement performed on the PRP. Since the PPP has only a low platelet concentration, it is usually a clear fluid and has a maximum transmittance. The transmittance measured on the PRP is usually correlated with this maximum transmittance. Only this procedure makes it possible in the prior art to interpret the LTA measurement meaningfully and in particular to be able to assess the maximum extent of the aggregation along with the speed of the aggregation change.

Taking an additional amount of blood as required to obtain the PPP sample may be a burden for the subject. This is especially true for newborns or infants who naturally have a small amount of blood, or else for patients from whom only a limited amount of blood is able to be taken due to pre-existing conditions. In addition, additional work and additional consumables are required to provide the PPP sample.

SUMMARY

Against this background, the object of the present invention is to provide a method for creating a database for determining a virtual reference value for an LTA measurement, a method for determining a virtual reference value for performing an LTA measurement using the created database, and a method for performing an LTA measurement, all of which deliver reliable results with less effort. This object is achieved with the aid of the features of the independent claims. Advantageous embodiments are specified in the dependent claims.

The method according to the invention for creating a database for determining a virtual reference value for an LTA measurement comprises the following steps:
a. providing platelet-rich plasma (PRP) of a reference blood sample;
b. performing a light transmission measurement with a first light wavelength and a second light wavelength, different from the first, on the PRP of the reference blood sample;
c. providing platelet-poor plasma (PPP) of the reference blood sample;
d. performing a light transmission measurement on the PPP in order to determine a PPP reference value;
e. assigning the measurement result of step d to the measurement results of step b in a database;
f. repeating steps a to e for a plurality of reference blood samples.

Some of the terms used in this description will first of all be explained. The method according to the invention requires the provision of platelet-rich and platelet-poor plasma of a blood sample. The provision may take place in a manner that is generally known, for example as described in the document "Leitinie-Thrombozytopathien [Thrombocytopathy Guidelines], Version 2.1 (AWMF Register no. 086-003, update 2/2018)". In this case, a defined amount of a suitable anticoagulant (for example sodium citrate) is in particular added to the blood sample in order to prevent blood clotting.

When performing a light transmission measurement on the PRP or on the PPP of the blood sample, a light beam of a predefined intensity is preferably directed onto a volume of the PRP or the PPP that is usually located in a transparent container, wherein the intensity of the light beam is measured after it has passed through the volume. The ratio of the initially predefined intensity to the intensity after passing through gives a transmittance, which may represent the result of the light transmission measurement. In the case of a light transmission measurement on the PPP, the transmittance may form the PPP reference value.

When light transmission measurements are performed with a first wavelength and with a second wavelength, these measurements may be performed in temporal succession or else simultaneously on different partial volumes of the volume under examination.

Two wavelengths are considered to be different within the scope of the present description if they differ by at least 10 nm. In one embodiment, the first wavelength differs from the second wavelength by at least 50 nm, preferably by at least 100 nm, more preferably by at least 200 nm. The first wavelength may be in a range between 300 nm and 500 nm, and is preferably between 345 nm and 465 nm, more preferably between 385 nm and 425 nm. Furthermore, the second wavelength may be in a range between 500 nm and 800 nm, and is preferably between 550 nm and 700 nm, more preferably between 600 nm and 640 nm.

The light transmission measurements carried out on the PRP may be performed, within the scope of the invention, with monochromatic light having at least the abovementioned wavelength difference or within the abovementioned ranges. It is also possible, within the scope of the invention, for light beams formed by a superposition of multiple light wavelengths to be used for the light transmission measurement. In this case, the wavelength of the light beam is given by an average value (preferably weighted according to intensity) of the wavelengths contained in the light beam. In this respect, the wavelength difference between two light beams is predefined by the difference between the average values of the light beams. When reference is made to the "light of a wavelength", within the scope of the present description, this may also mean a corresponding light beam the wavelength average value of which is this wavelength.

Within the scope of the invention, a light transmission measurement with at least two different wavelengths is performed on the PRP of a reference blood sample, from which it is possible in particular to determine a transmittance. In addition, a reference value of the light transmission is determined on the PPP of the reference blood sample in a manner generally known from the prior art (hereinafter also referred to as PPP reference value). Within the scope of the invention, it has been recognized that there is a statistically significant relationship between the measured values obtained on the PRP with the at least two different wavelengths and the PPP reference value that becomes apparent when the values stored in the database for a plurality of reference blood samples are evaluated. This statistical relationship makes it possible, once the database has been created, to use said database to determine a virtual reference value for another blood sample of a patient to be examined, this virtual reference value being a reliable estimate of the PPP reference value, without the additional need to obtain and measure a PPP sample from the same patient. By way of example, a mathematical relationship between the measured values obtained on the PRP of a blood sample to be examined and the virtual reference value may be determined from the database. This is explained in more detail below in conjunction with the method for determining a virtual reference value and the method for performing an LTA measurement. As an alternative, a virtual reference value for a PPP reference value may also be determined from the database by other means, in particular with the aid of static methods that are generally known (possibly using artificial intelligence). Such methods are generally known to a person skilled in the art. The core of the invention is the finding that the method steps according to the invention make it possible to create a database containing sufficient information to determine the virtual reference value. Owing to the database according to the invention, it is therefore possible to dispense with an additional blood sampling in order to obtain a PPP sample and avoid the resulting effort.

It has been recognized within the scope of the invention that, for a specific blood sample, both the PPP reference value and the measured values obtained with different wavelengths on the PRP are dependent on the physiological state of the blood sample, that is to say in particular on the type and concentration of substances contained in the blood sample, which influence the transmittance both of the PPP sample (and thus the PPP reference value) and of the PRP sample. Such substances may be for example hemoglobin, ceruloplasmin, bilirubin, lipoproteins, or else other substances supplied by medicines. The inventors assume that there are certain substances that influence transmittance as a function of light wavelength. The use of at least two different light wavelengths thus results, within the database, in a correlation between the measured values determined on the PRP and the PPP reference value, since both the PRP measured values and the PPP reference value are influenced in a predetermined manner by the type and/or concentration of the substances contained in the blood sample. Once the database has been created, it is therefore possible to draw conclusions about the PPP reference value when examining further blood samples solely by measuring the PRP with the different wavelengths and if necessary using the database (or a mathematical relationship obtained therefrom), without the need to obtain an additional PPP sample.

In one preferred embodiment, the method for creating the database comprises the following further steps:
  g. adding a predefined amount of an activator to the PRP of the reference blood sample after performing the measurement according to step b;
  h. repeating the measurement according to step b after adding the activator and before introducing an aggregation triggered by the activator;
  i. assigning the measurement result of step h to the measurement result of step d in the database;
  j. repeating steps g to i for the plurality of reference blood samples.

The term "activator" in this case denotes a reagent or a plurality of reagents that is/are configured to trigger platelet aggregation after addition to the PRP. The activator may comprise one or more reagents selected from the group comprising ristocetin, arachidonic acid, adenosine triphosphate (ATP), epinephrine (adrenaline), collagen, thrombin receptor-activating peptides (TRAPs). After adding the activator, the aggregation begins with a time delay. The platelets remain in the activated state for a certain time period, and there is still no increase in light transmission triggered by cross-linking of the platelets. Preferably, the repeated measurement of step h is performed during this time period, that is to say before the actual aggregation takes place. The light transmission measurement after the addition of the activator according to step h is preferably performed in a time period between 0 and 10 s, preferably between 0 and 5 s after the addition of the activator, wherein, preferably, a temporal average value is formed over a time period between 1 s and 6 s, preferably between 3 s and 5 s, in order to acquire a transmission value. The light transmission measurement before the addition of the activator preferably takes place immediately before the addition of the activator, for example in a time period between 0 s and 10 s before the addition of the activator. The mixing ratio between a PRP volume and the volume of the activator that is added to the PRP volume according to step g is usually 9:1, but may also be for example between 20:1 and 2:1, preferably between 15:1 and 4:1, more preferably between 7:1 and 11:1.

In the embodiment described above, the light transmission measurement is performed with two light wavelengths both before and immediately after the addition of a predefined amount of the activator. It turned out that the additionally obtained measured values may be used to draw even more accurate and meaningful conclusions about a PPP reference value. In particular, it has been recognized that the addition of a predefined amount of the activator to the PRP induces an initial change in light transmission that is dependent on the individual PRP sample, which change may be a decrease or else an increase in light transmission. This initial change likewise exhibits a dependence on the physiological state of the blood sample, and in particular on the substances therein. In the described embodiment, additional information is thus added to the database, which additional information enables an improved statistical conclusion about a PPP reference value.

In one embodiment of the invention, provision is made, in method step g, for a first activator to be used in a first reference blood sample and a second activator, different from the first, to be used in a second reference blood sample. This makes it possible to distinguish, within the database, between measured data that were obtained by way of different activators. If a virtual reference value of a blood sample to be examined is determined later using a specific activator, then it is possible, within the database, to access measurement results that were acquired on reference blood samples using the same activator (or mathematical relationships determined therefrom). If it is to be expected that the different activators do not induce different measurement results, the measurement results obtained based on different activators may also be combined in the database or used together to determine a mathematical relationship.

The light transmission measurements of step b and/or of step h may be performed with at least three mutually different light wavelengths. In particular, the light of the first wavelength may have a wavelength in the range between 380 nm and 420 nm, preferably between 400 nm and 410 nm. Light of the second wavelength may have a wavelength in the range between 500 nm and 550 nm, preferably between 520 nm and 530 nm. Light of a third wavelength may have a wavelength in the range between 620 nm and 700 nm, preferably between 620 nm and 630 nm. It turned out that the use of three wavelengths further increases the accuracy with which it is possible to draw a conclusion about a PPP reference value. The three wavelengths are preferably used both for the measurement before the addition and for the measurement after the addition of the activator.

In one advantageous embodiment, the plurality of reference blood samples contains a first reference blood sample and a second reference blood sample, wherein the first reference blood sample contains at least one first substance that is not contained, or is contained in a lower concentration, in the second reference blood sample. By way of example, the concentration of the substance in the first reference blood sample may be greater than the concentration of the substance in the second reference blood sample by a factor of more than 1.5, preferably more than 3, more preferably more than 5. Differences in concentration by a factor of 20, for example, are also possible. The first substance may preferably be selected from the group consisting of hemoglobin, ceruloplasmin, lipoprotein, triglycerides, bilirubin. The first substance may also be dyes or ingredients derived from medicines or food, or the degradation products thereof. If the reference blood samples differ in terms of their substances, the database covers a broader basis of different physiological states of the blood samples. Preferably, in order to create the database, use is made of a plurality of reference blood samples (for example more than 5, preferably more than 10, more preferably more than 20) that each differ from one another in pairs in terms of the type and/or concentration of at least one of their substances, for example by the differences in concentration described above. It is also possible for the database to be created using reference blood samples that each differ from one another in pairs by more than one, preferably more than 2, more preferably more than 5 substances, wherein the difference may be given by the abovementioned difference in concentration. This further improves the accuracy with which statistical conclusions may be drawn from the database.

Provision may be made for the PRP volume of a reference blood sample to be divided into a plurality of partial volumes, wherein the method according to the invention is performed on each of these partial volumes, wherein a respective average value of the determined measured values is formed over the number of partial volumes and recorded in the database. Such averaging makes it possible to further increase statistical accuracy.

In one embodiment, the first substance is added manually to the first reference blood sample. It is also possible to add the substance to different reference blood samples in different predefined concentrations. This has the advantage that the influence of a substance on the measured values determined within the scope of the invention is able to be systematically captured and recorded in the database. In particular, measurement series may be carried out with a plurality of reference blood samples, in which the substance is added to different reference blood samples in a plurality of different concentrations and/or in which a plurality of different substances are added, possibly in different concentrations, to different reference blood samples.

It is also possible in principle for at least some of the reference blood samples used to perform the method according to the invention to be obtained from subjects in whom it may be expected, for example due to pre-existing conditions or the intake of medicines or other influences, that the reference blood samples will differ from one another in terms of the type and/or the concentration of the substances contained therein.

The invention furthermore relates to a method for determining a virtual reference value for performing an LTA measurement on the PRP of a blood sample to be examined using a database according to the invention. The method comprises the following steps:
 a. providing PRP of the blood sample to be examined;
 b. performing a light transmission measurement with a first light wavelength and a second light wavelength, different from the first, on the PRP of the blood sample to be examined;
 c. using the measurement results obtained by step b and the database according to the invention to determine the virtual reference value of the blood sample to be examined.

After a database according to the invention has been created, what is referred to as a virtual reference value may be determined using the method described above for a further blood sample to be examined. The virtual reference value here is an estimate of the PPP reference value determined based on the database and the measurements carried out on the PRP. Using the virtual reference value, it is possible to meaningfully interpret a subsequently performed LTA measurement without the need to obtain a PPP sample from the same patient.

Preferably, the method for determining a virtual reference value comprises the following further steps:
d. adding a predefined amount of an activator to the PRP of the blood sample to be examined after performing the measurement according to step b;
e. repeating the measurement according to step b after adding the activator to the PRP of the blood sample to be examined and before introducing an aggregation triggered by the activator;
f. incorporating the measurement results obtained by step e into the determination of step c.

The provision of the PRP according to step a and the performing of the light transmission measurements according to steps b and/or e may be carried out in the same way as described above in conjunction with the method for creating the database. Provision may be made in particular for (at least substantially) the same light wavelengths or light wavelength ranges to be used and/or (at least substantially) the same ratio between the PRP volume and the volume of the added activator to be used for the measurements. The method for determining a virtual reference value may be further developed in this regard by the features already described above in conjunction with the method for creating a database. It may thereby be ensured that the measurement results are captured under the same conditions, or at least conditions that are as similar as possible, as when the database is created. The conclusion that is drawn based on the measurement results captured on the blood sample to be examined may thereby be achieved with high accuracy.

In the simplest case, the virtual reference value may be determined by way of a comparison between the measurement results of the blood sample to be examined (obtained by steps b and where applicable e) and the measurement results contained in the database. If the database contains measurement results for a reference blood sample that are identical or substantially identical to the measurement results for the blood sample to be examined, then the PPP reference value present in the database in relation to this reference blood sample may be used as a virtual reference value.

In many cases, however, the database will not contain a record of a reference blood sample that matches the record of the blood sample to be examined to a sufficient extent. In addition, a single record contained in the database may in principle also be impacted by a measurement error, meaning that resorting to a single record to ascertain the virtual reference value may lead to errors. Provision is therefore preferably made for a mathematical relationship based on the database to be established, this relationship having the measurement results obtained on the blood sample to be examined as input variables and the virtual reference value of the blood sample to be examined as output variable. It has in particular been shown that the virtual reference value virtPPP (sometimes also referred to as virtREF in the description) may be indicated as a mathematical function of the measured values:

$$\text{virtPPP}=\text{virtPPP}(xd1, xd2, xd3, xd4), \text{ wherein}$$

xd1: is the transmittance measured on the PRP of the blood sample to be examined at the wavelength $\lambda 1$ before the addition of the activator,
xd2: is the transmittance measured on the PRP of the blood sample to be examined at the wavelength $\lambda 2$ before the addition of the activator,
xd3: is the transmittance measured on the PRP of the blood sample to be examined at the wavelength $\lambda 1$ after the addition of the activator,
xd4: is the transmittance measured on the PRP of the blood sample to be examined at the wavelength $\lambda 2$ after the addition of the activator,
$\lambda 1$: is the first wavelength, and
$\lambda 2$: is the second wavelength.

The mathematical relationship or the function virtPPP (xd1, xd2, xd3, xd4) may be obtained from the database by way of statistical adjustment methods that are generally known from the prior art.

In one advantageous embodiment, as part of the mathematical relationship, the ratios $V1=xd1/xd2$, $V2=xd3/xd4$, and $V3=V2/V1$ are determined and used for the calculation of the virtual reference value.

If more than two light wavelengths have been used to create the database and the measurement of the blood sample to be examined, the function may be extended accordingly by way of statistical adjustment methods that are generally known in the prior art.

The invention furthermore relates to a method for performing an LTA measurement on a blood sample to be examined, comprising the following steps:
a. performing the method according to the invention for determining a virtual reference value of the blood sample to be examined,
b. performing an LTA measurement on the blood sample to be examined using the virtual reference value.

The light transmission aggregometry measurement may in particular follow the method for determining the virtual reference value immediately in time. If an activator has already been added when determining the reference value, the aggregation caused thereby may be captured as part of the subsequent LTA measurement. The activator is preferably designed such that it is suitable for an LTA measurement. The LTA measurement following the method for determining the virtual reference value may in principle take place with a single wavelength or else with multiple wavelengths, which are channeled alternately through a volume of the PRP or simultaneously through different partial volumes of the PRP.

The present invention furthermore relates to a device for determining a virtual reference value for performing an LTA measurement on the PRP of a blood sample to be examined, comprising an illumination module for selectively emitting light of a first light wavelength and of a second light wavelength different from the first, a sample receptacle for the introduction of a PRP sample such that the light from the illumination module passes through the PRP, a light sensor that is designed to capture the light that has passed through the PRP, and a control module that is designed to drive the device such that the following steps are carried out:
a. performing a light transmission measurement with a first light wavelength and a second light wavelength, different from the first, on the PRP of the blood sample to be examined;
b. using the measurement results obtained by step a and a database according to the invention to determine a virtual reference value of the blood sample to be examined.

In one preferred embodiment, the device comprises an applicator for automatically adding a predefined amount of an activator to the PRP, wherein the control module is designed to drive the device such that the following steps are carried out:

c. adding a predefined amount of an activator to the PRP of the blood sample to be examined after performing the measurement according to step a;
d. repeating the measurement according to step a after adding the activator to the PRP of the blood sample to be examined and before introducing an aggregation triggered by the activator;
e. incorporating the measurement results obtained by step d into the determination of step b.

The device may in particular have a computing module that is designed to access a mathematical relationship based on a database according to the invention and to determine the virtual reference value on the basis of the mathematical relationship and of the measured values obtained in step a or in steps a and d. The mathematical relationship may be stored in particular in the computing module.

The device according to the invention may be further developed by further features that have been described in conjunction with the method for creating a database, the method for determining a virtual reference value and/or the method for performing a light transmission aggregometry measurement.

BRIEF DESCRIPTION OF THE DRAWINGS

Preferred exemplary embodiments of the invention are explained in detail below with reference to the accompanying drawings, in which.

DETAILED DESCRIPTION

Figure 1:
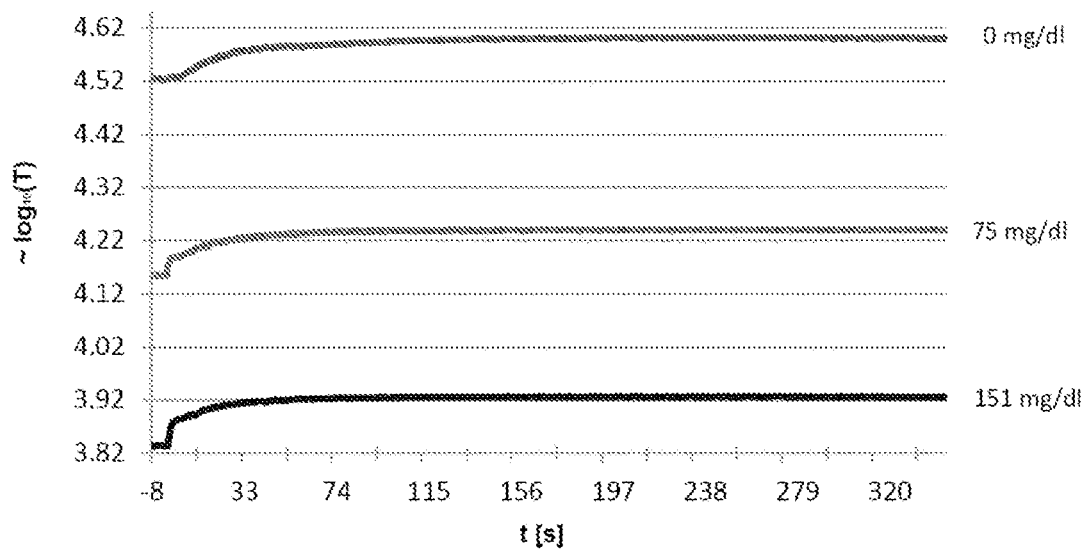
FIG. 1: shows examples of light transmission measurements that were performed on the PRP of three reference blood samples with a first wavelength.

FIG. 1 shows three exemplary light transmission measurements over time that were performed on the PRP of three different reference blood samples. The change in the measured value of an intensity meter is plotted as a function of time. The measured value is proportional to the common logarithm of the transmittance (the transmittance is referred to below using the letter T). An increase in the measured value thus corresponds to an increase in the transmittance. The measurements span the time period t=−8 s to t=6 min, wherein, at the time t=0 s, the activator adenosine diphosphate (ADP) was added at a volume ratio of 1:9 to the respective PRP sample (one part ADP, 9 parts PRP). The measurements were performed with a wavelength of $\lambda 1 = 625$ nm. Reference blood samples 1 to 3 differ from one another only in the type of substance added manually to the respective sample. During reference blood sample 1, no substance was added manually; intralipids were added to reference blood samples 2 and 3 at concentrations of 75 mg/dl and 151 mg/dl, respectively. It may be seen in FIG. 1 that the addition of the intralipids leads to a lower absolute value of the transmittance.

Figure 2:
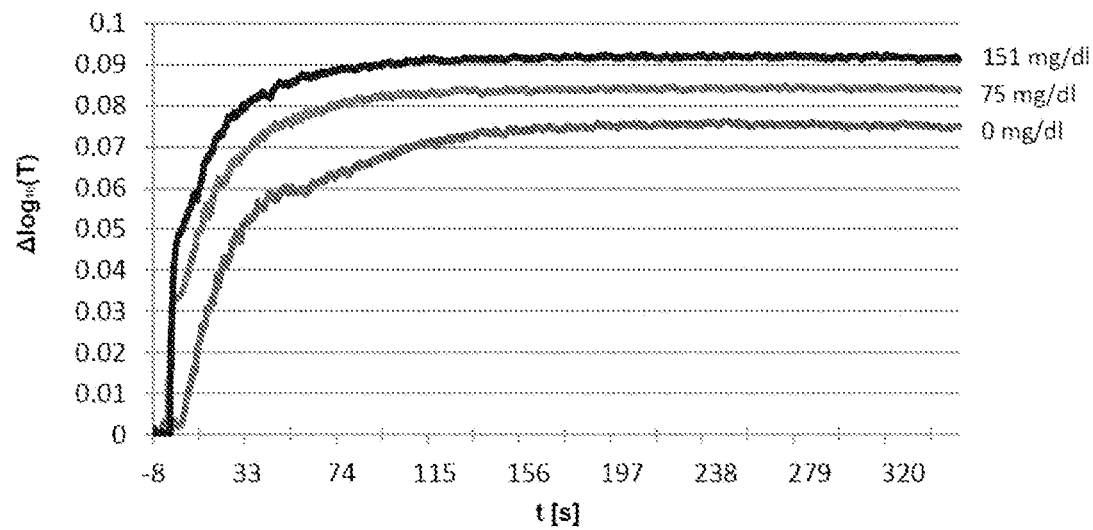
FIG. 2: shows the light transmission measurements from FIG. 1, wherein the measurement curves were shifted to the zero point at the time t=−8 s.

FIG. 2 shows the measurements from FIG. 1, wherein the curves have been shifted to the zero point in order to make the changes in the transmittance clearer. It may be seen that the transmittance of reference sample 1 hardly changes, or even decreases, shortly after the addition of the activator (between t=0 and t=10 s). During this time period, the platelet activation process begins without any aggregation already having taken place. After the end of the time period, the platelet cross-linking begins at around t=10 s, and aggregates form in the PRP, as a result of which the transmittance increases over time. After around t=150 s, a maximum transmittance is reached, which then hardly changes.

For reference samples 2 and 3, on the other hand, it is possible to see a sudden change by $\Delta(\log_{10} T)=0.03$ and by $\Delta(\log_{10} T)=0.05$, respectively, at the time t=0. For these reference blood samples too, the aggregation then begins (from around t=10 s) and the transmittance continues to increase.

The absolute value of the change in the transmittance has no significance per se, since it depends for example on the concentration of platelets contained in the sample and on the concentration and type of other substances contained therein. For this reason, in the prior art, it is necessary to determine a respective PPP reference value through a light transmission measurement on the PPP of the same blood sample and to correlate the measured values obtained on the PRP with this measured PPP reference value. Such PPP reference values were determined, in the reference blood samples shown above, in a manner known from the prior art.

Figure 3:
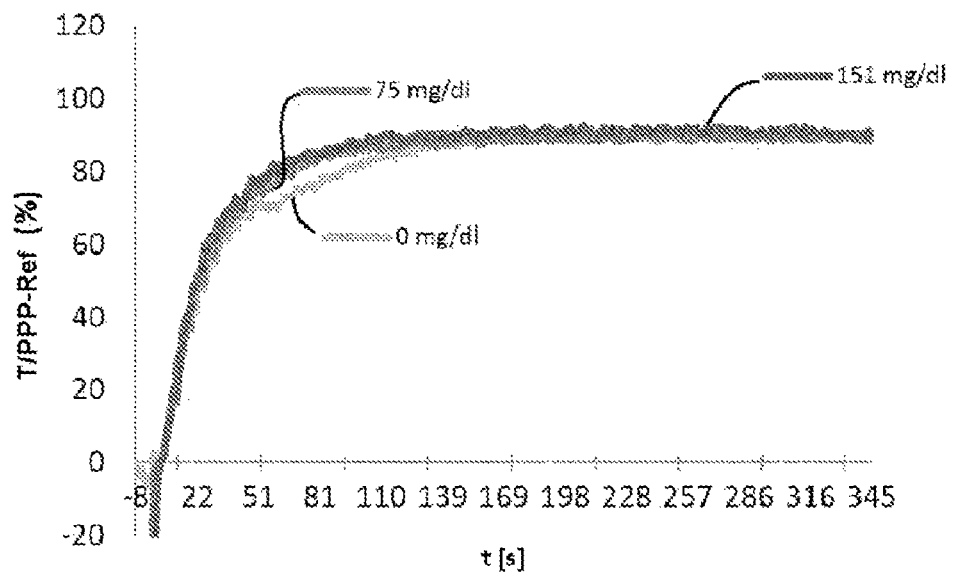
FIG. 3: shows the ratio between the transmittances shown in FIG. 2 and the respective PPP reference value of the respective reference blood sample over time.

FIG. 3 shows the corresponding ratio of the transmittances of reference blood samples 1 to 3 to the respective PPP reference value overtime. It may be seen that the ratio over time approaches a value of around 85 for all three samples. From the measured data shown in FIG. 3, it is possible to draw conclusions about the functionality of the platelets.

The method according to the invention for creating a database is explained below by way of example with reference to the measured data shown in FIGS. 1 to 3. In addition to the transmission measurements shown in FIGS. 1 to 3, a respective light transmission measurement with the wavelength $\lambda 2=405$ nm was performed on the PRP of the same reference blood samples shortly before the addition of the activator (at t=−3 s) and shortly after the addition of the activator (by forming an average value in the time period between t=2 s and 6 s). By way of example, the following measurement results were obtained for reference blood sample 1:

the transmittance at the wavelength $\lambda 1$ before the addition of the activator at the time t=−3 s: xd1=0.82676788;

the transmittance at the wavelength $\lambda 2$ before the addition of the activator at the time t=−3 s: xd2=0.532220558;

the transmittance at the wavelength $\lambda 1$ after the addition of the activator, obtained by averaging in the time period between t=2 s and t=6 s: xd3=0.840990463;

the transmittance at the wavelength $\lambda 2$ after the addition of the activator, obtained by averaging in the time period between t=2 s and t=6 s: xd4=0.551279411, and the PPP reference value measured on the PPP of the reference blood sample: PPP-Ref=1.0228.

The values xd1, xd2, xd3, xd4 and the PPP reference value were added to a database. Corresponding values were also determined for reference blood samples 2 and 3 and were likewise added to the database. The database is illustrated in Table 1 below.

TABLE 1

| | Sample no. | | |
|---|---|---|---|
| | 1 | 2 | 3 |
| added substance | — | intralipid 75 mg/dl | intralipid 151 mg/dl |
| xd1 | 0.82676788 | 0.362703212 | 0.166929278 |
| xd2 | 0.532220558 | 0.092530236 | 0.027191926 |
| xd3 | 0.840990463 | 0.38363385 | 0.188179259 |
| xd4 | 0.551279411 | 0.102101591 | 0.027871212 |
| PPP-Ref | 1.0228 | 0.4433 | 0.2118 |
| virtREF | 1.0409 | 0.460 | 0.205 |

Corresponding measured values were captured for further reference blood samples 4 to 7 and likewise added to the database. Reference blood samples 4 to 7 differed from one another only in terms of the respective substances added manually to the PRP. The substances and the concentration thereof are listed, together with the captured measured values, in Table 2 below.

TABLE 2

| | sample no. | | | |
|---|---|---|---|---|
| | 4 | 5 | 6 | 7 |
| added substance | — | 15 mg/dl bilirubin | 568 mg/dl hemoglobin | 372 mg/dl triglycerides |
| xd1 | 0.91048 | 0.881060 | 0.852417 | 0.557092 |
| xd2 | 0.56510 | 0.017670 | 0.129883 | 0.214720 |
| xd3 | 0.92432 | 0.88447 | 0.862035 | 0.593829 |
| xd4 | 0.58818 | 0.018583 | 0.151792 | 0.236192 |
| PPP-Ref | 1.0184 | 1.0160 | 0.9520 | 0.6849 |
| virtREF | 1.01991 | 1.01034 | 0.9831 | 0.69194 |

Within the database, it is possible to recognize patterns that are based on the influence of the additionally added substances. Comparing the transmission values reveals for example that the addition of a substance may have a specific influence both on the determined transmission values and on the measured PPP reference values. By way of example, a comparison of the values xd1 and xd2 of samples 4 to 6 shows that a change in transmittance triggered by the addition of bilirubin or hemoglobin is significantly more pronounced at the wavelength $\lambda 2$ than at the wavelength $\lambda 1$.

Another recognizable pattern is for example that, for sample 1, the addition of the activator causes only a small change between the transmission values xd1 and xd3, while the change for samples 2 and 3 (that is to say with an increase in intralipid concentration) increases significantly (see FIG. 2). At the same time, the addition of the substances leads to a more or less pronounced change in the PPP reference value.

After the measurements explained above by way of example have been performed on a large number of reference blood samples and recorded in the database, the type of patterns described above leads to statistically significant relationships that make it possible to establish a mathematical relationship in order to determine a virtual reference variable.

One example of a mathematical relationship is explained below: The variables:

$$V1 = xd1/xd2,$$

$$V2 = xd3/xd4,$$

$$V3 = V2/V1,$$

$$Ve = (V1+V2)/e^{V3} \text{ and}$$

$$X^{xdPIP} = xd4 + xd3 - xd2 - xd1$$

are determined. In addition, the variable $$X^{vPIP} = (1-xd3) \times (-\log_{10}(xd3)) \times (V1+Ve)/e^{Ve}$$

is determined. Based on the variables referenced above, a preliminary virtual reference variable 1virtPPP may be determined as follows:

$$1\text{virtPPP} = 1 + X^{xdPIP} - X^{vPIP}.$$

In addition, the factor $$F\iota = xd3/1\text{virtPPP}$$

is calculated. It turned out that, for those PRP samples in which the value of the factor F1 is less than a threshold value (in the present example F1<1.19), the preliminary virtual reference variable 1virtPPP is a good estimate for the PPP reference value.

If the factor F1 is greater than the threshold value (in the present example, that is to say F1>1.19), then a corrected virtual reference value 2virtPPP is determined as follows:

$$2\text{virtPPP} = 1.26 \times F1^{-1.134}.$$

For those PRP samples in which the factor is F1>1.19, the corrected virtual reference value 2virtPPP is a good estimate for the PPP reference value. The mathematical relationship, reproduced below, for ascertaining the virtual reference value virtPPP was thus determined from the database in this case:

$$\text{virtPPP} = \begin{cases} 1\text{virtPPP} = 1 + X^{xdPIP} - X^{vPIP}, & \text{if } F1 < 1.19 \\ 2\text{virtPPP} = 1.26 \times F1^{-1.134}, & \text{if } F1 > 1.19 \end{cases}$$

The virtual reference values virtPPP thereby determined for reference samples 1 to 6 are indicated in Tables 1 and 2 above. The tables show that there is a good match with the measured PPP reference values (PPP-Ref).

Figure 4:
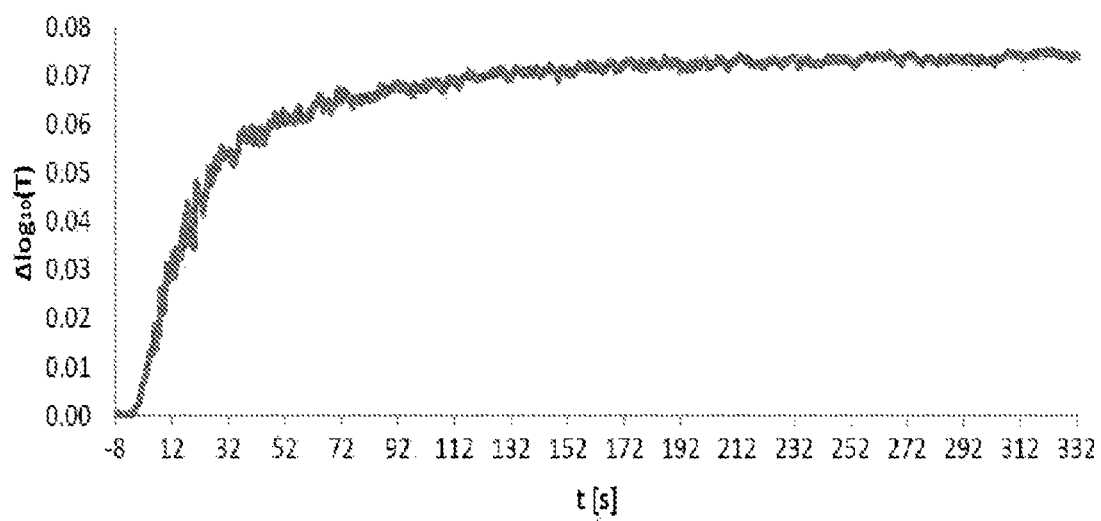
FIG. 4: shows one example of an LTA measurement that was performed on the PRP of a blood sample to be examined.

FIG. 4 shows an LTA measurement on the PRP of a blood sample to be examined, which was performed under the same measurement conditions as the measurements shown in FIGS. 1 and 2 in a time period between t=−8 s and t=6 min, wherein the measurement curve is shifted to the zero point at the time t=−8 s. At the time t=0 s, the activator ADP was added to the PRP in a ratio of 9:1. The following transmission values xd1, xd2, xd3, xd4 were ascertained for the wavelengths $\lambda 1=625$ nm, $\lambda 2=405$ nm in the manner already described above before and after the addition of the activator, respectively:

$$xd1=0.698934,\ xd2=0.257505,\ xd3=0.726952,$$
$$xd4=0.280035.$$

The mathematical relationship described above was used to calculate the abovementioned intermediate values as follows:

| V1 | V2 | V3 | $X^{xdPIP}$ | $V^e$ | $X^{vPIP}$ |
|---|---|---|---|---|---|
| 2.714 | 2.596 | 0.956 | 0.05055 | 2.04055443 | 0.0264134 |

The provisional virtual reference value was:

1virtPPP=1.0259

In addition, the factor was determined.

$F1=1.411$.

Since the factor exceeds the value of 1.19, the resulting virtual reference value was:

virtPPP=2virtPPP=1.26×$F1^{-1.134}$=0.857514.

Figure 5:
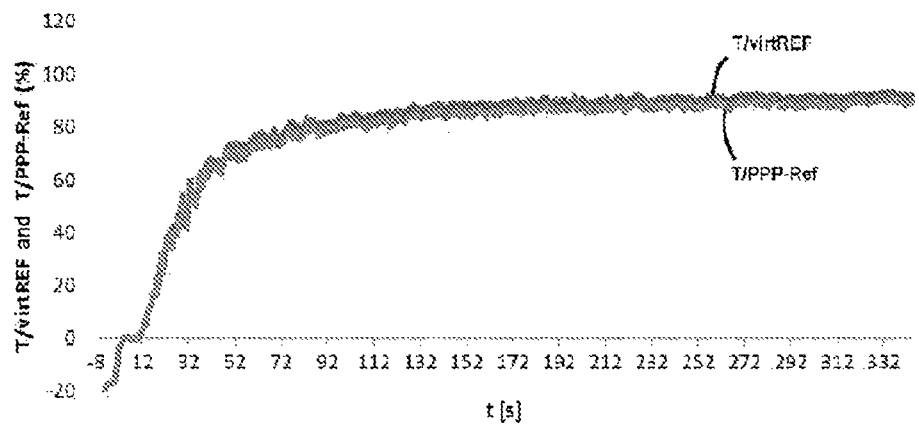
FIG. 5: shows the ratio between the transmittance shown in FIG. 4 and the virtual reference value and also the measured PPP reference value of the blood sample to be examined over time.

For control purposes, a PPP reference value PPP-Ref=0.8869 was ascertained on the PPP of the same blood sample to be examined in a manner known from the prior art. The virtual reference value is thus a good estimate for the PPP reference value. FIG. 5 shows the ratio of the measured transmission value to the virtual reference value virtREF and to the measured reference value PPP-Ref over time. Owing to the good match between the values virtREF and PPP-Ref, the two measurement curves shown in FIG. 5 are almost identical.

Figure 6:
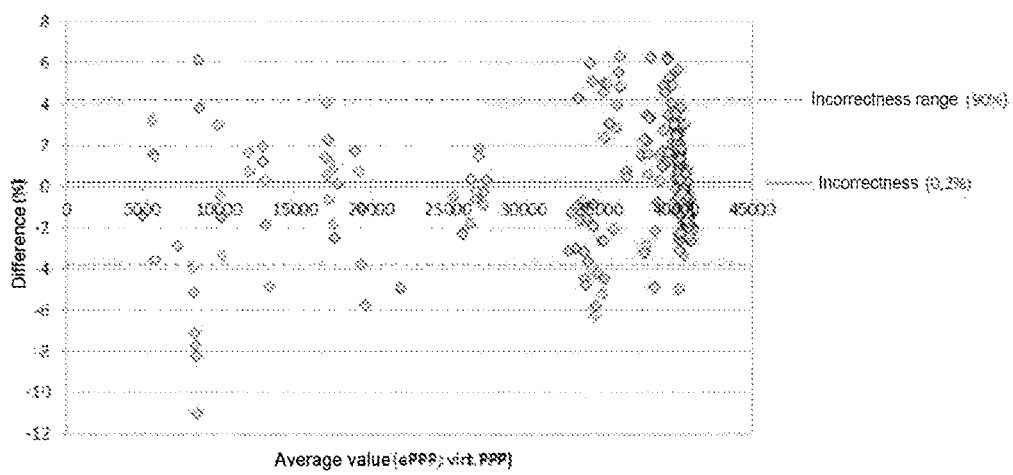
FIG. 6: shows a comparison between measured PPP reference values and virtual reference values for a large number of blood samples to be examined, as determined using the method according to the invention.
Figure 7:
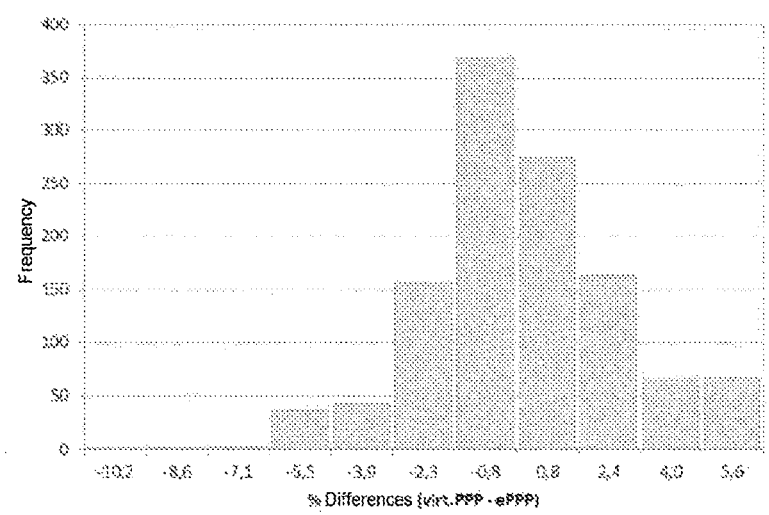
FIG. 7: shows a statistical evaluation of the results shown in FIG. 6.

In the manner described above and using the mathematical relationship determined based on the database according to the invention, a respective virtual reference value (referred to as virt.ppp in the figure) was determined for a plurality of blood samples to be examined and, in addition, a PPP reference value (referred to as ePPP in the figure) was measured in a manner known from the prior art in order to compare the virtual reference value in each case with the measured PPP reference value. For this purpose, the average value of the measured PPP reference value and the virtual reference value was determined and the percentage difference between the variables was ascertained. FIG. 6 shows this difference as a function of the average value, wherein, in the scale shown, an average value of 40000 corresponds approximately to a PPP reference value of 1. It turns out that, using the method according to the invention, it was possible to calculate a virtual reference value for a majority of the examined blood samples, which reference value represents a very good estimate for the PPP reference value actually measured. As illustrated in FIG. 7, the difference, in 90% of cases, is within a small error interval of around +/−4%. The suitability of the method according to the invention for ascertaining a good estimate for the PPP reference value was thus confirmed.

Figure 8:
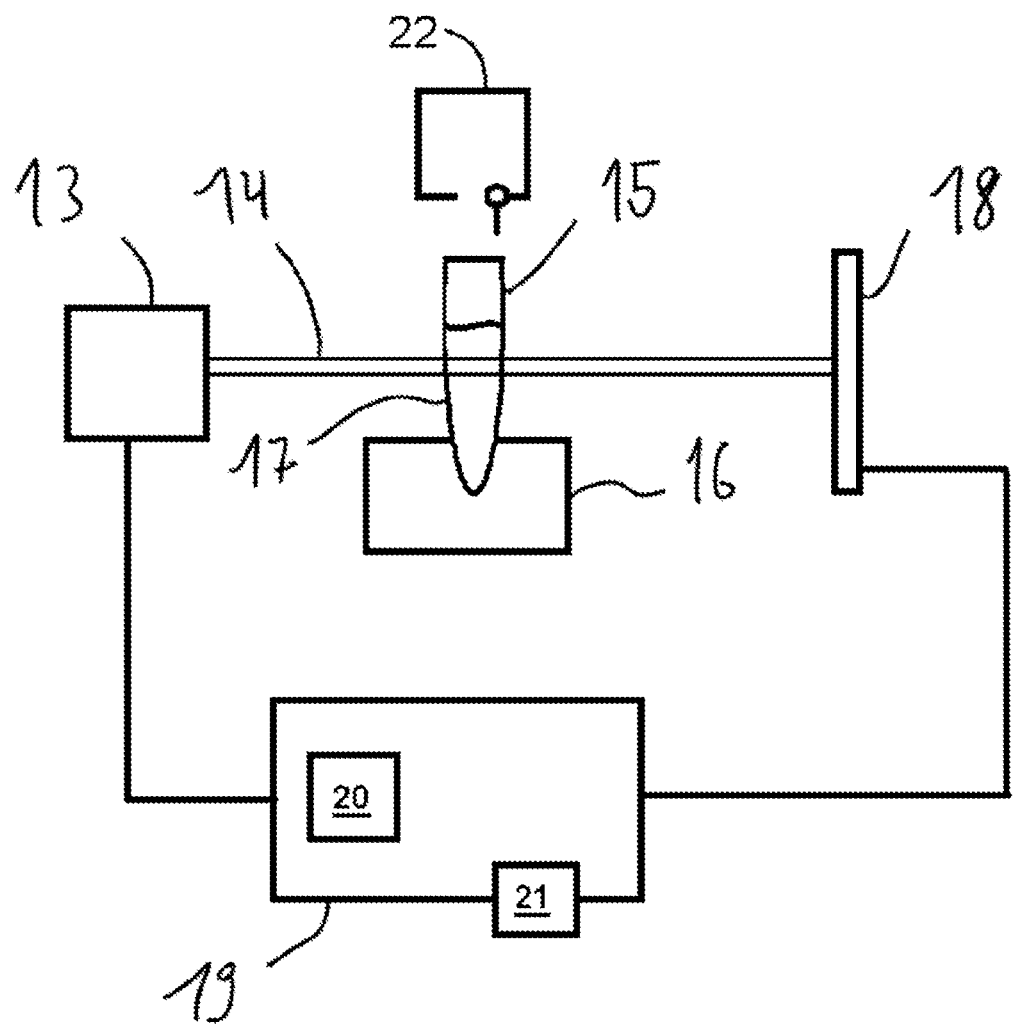
FIG. 8: shows a schematic view of a device according to the invention for determining a virtual reference value.

FIG. 8 shows a device according to the invention for determining a virtual reference value for performing an LTA measurement. The device comprises an illumination module 13, which is designed to emit light beams 14 of a first light wavelength of 405 nm and of a second light wavelength of 625 nm and with a predefined intensity in each case. The device furthermore comprises a sample holder 16 into which a transparent cuvette 15 is able to be introduced manually or else automatically. The cuvette 15 contains PRP 17 of a blood sample to be examined. The sample holder is arranged such that the light beams 14 impinge on a subregion of the cuvette 15 and pass through the PRP 17 arranged therein. The light beams 14 that have passed through the PRP 17 then impinge on a sensor 18, which captures the intensity of the light beams and forwards same to a control module 19. The device furthermore has an applicator 22 that is designed to add a predefined amount of an activator to the PRP 17. The illumination module 13 and the applicator 22 are controlled by the control module 19 so as to perform the method according to the invention, wherein the respective measured transmission values xd1, xd2, xd3 and xd4 are simultaneously captured by the sensor and stored in the control module. The control module 19 furthermore comprises a computing module 20 in which the mathematical relationship according to the invention is stored. Using the mathematical relationship and the measured transmission values, the computing module 20 determines a virtual reference value for the LTA measurement.

As an alternative or in addition, provision may also be made for a network interface 21 that transmits the measured values xd1 to xd4 captured by the sensor to an external computing module via a data connection, wherein the determination of a virtual reference value is in this case taken over by the external computing module.

The invention claimed is:

1. A method for creating a database for determining a virtual reference value for a PPP reference value of a light transmission aggregometry measurement, comprising the following steps:
   a) providing platelet-rich plasma (PRP) of a reference blood sample;
   b) performing a light transmission measurement with a first light wavelength and a second light wavelength, different from the first, on the PRP of the reference blood sample, wherein the first wavelength is in a range between 300 nm and 500 nm and the second wavelength is in a range between 500 nm and 800 nm, wherein the first light wavelength differs from the second light wavelength by at least 50 nm;
   c) providing platelet-poor plasma (PPP) of the reference blood sample;
   d) performing a light transmission measurement on the PPP in order to determine a PPP reference value;
   e) assigning the measurement result of step d to the measurement results of step b in a database;
   f) repeating steps a to e for a plurality of reference blood samples that each differ from one another in pairs in terms of the type and/or concentration of at least one of their substances.

2. The method of claim 1, wherein the first and/or second wavelength satisfy at least one of the following features:
   the first wavelength differs from the second wavelength by at least 100 nm, preferably by at least 200 nm,
   the first wavelength is in a range between 345 nm and 465 nm, more preferably between 385 nm and 425 nm, and
   the second wavelength is in a range between 550 nm and 700 nm, more preferably between 600 nm and 640 nm.

3. The method of claim 1, comprising the following further steps:
   g) adding a predefined amount of an activator to the PRP of the reference blood sample after performing the measurement according to step b;
   h) repeating the measurement according to step b after adding the activator and before introducing an aggregation triggered by the activator;
   i) assigning the measurement result of step h to the measurement result of step d in the database;
   j) repeating steps g to i for the plurality of reference blood samples.

4. The method of claim 3, wherein the light transmission measurement according to step h is performed in a time period between 0 and 10 s, preferably between 0 and 5 s after the addition of the activator.

5. The method of claim 4, wherein, during the light transmission measurement according to step h, a temporal average value of the light transmission is formed over a time period between 1 s and 6 s, preferably between 3 s and 5 s.

6. The method of claim 1, wherein the light transmission measurements of step b are performed with at least three mutually different light wavelengths.

7. The method of claim 1, wherein the plurality of reference blood samples comprises a first reference blood sample and a second reference blood sample, wherein the first reference blood sample contains at least one first substance that is not contained in the second reference blood sample or is contained in the second reference blood sample in a concentration that is less by a factor of more than 1.5, preferably by a factor of more than 3, more preferably by a factor of more than 5 than the concentration of the first substance in the second reference blood sample, wherein the first substance is preferably selected from the group consisting of hemoglobin, ceruloplasmin, lipoprotein, triglycerides, bilirubin.

8. The method of claim 7, wherein the first substance of the first reference blood sample is added manually.

9. A method for determining a virtual reference value for a PPP reference value of a light transmission aggregometry measurement on the PRP of a blood sample to be examined using a database of claim 1, comprising the following steps:
   a) providing PRP of the blood sample to be examined;
   b) performing a light transmission measurement with a first light wavelength and a second light wavelength, different from the first, on the PRP of the blood sample to be examined;
   c) using the measurement results obtained by step b and the database to determine the virtual reference value of the blood sample to be examined.

10. The method of claim 9, furthermore comprising the following steps:
   d) adding a predefined amount of an activator to the PRP of the blood sample to be examined after performing the measurement according to step b;
   e) repeating the measurement according to step b after adding the activator to the PRP of the blood sample to be examined and before introducing an aggregation triggered by the activator;
   f) incorporating the measurement results obtained by step e into the determination of step c.

11. The method of claim 9, wherein a mathematical relationship based on the database is established, this relationship having the measurement results obtained on the blood sample to be examined as input variables and the virtual reference value of the blood sample to be examined as output variable.

12. A method for performing a light transmission aggregometry measurement on a blood sample to be examined, comprising the following steps:
   a) performing the method of claim 9 for determining the virtual reference value of the blood sample to be examined,
   b) performing a light transmission aggregometry measurement using the virtual reference value.

13. A device for determining a virtual reference value for performing an LTA measurement on the PRP of a blood sample to be examined, comprising an illumination module (13) for selectively emitting light of a first light wavelength and of a second light wavelength different from the first, a sample receptacle (16) for the introduction of a PRP sample (17) such that the light from the illumination module (13) passes through the PRP (17), a light sensor (18) that is designed to capture the light that has passed through the PRP (17), and a control module (19) that is designed to drive the device such that the following steps are carried out:
   a) performing a light transmission measurement with a first light wavelength and a second light wavelength, different from the first, on the PRP of the blood sample to be examined, wherein the first wavelength is in a range between 300 nm and 500 nm and the second wavelength is in a range between 500 nm and 800 nm, wherein the first light wavelength differs from the second light wavelength by at least 50 nm;
   b) using the measurement results obtained by step a and a database of claim 1 to determine a virtual reference value of the blood sample to be examined.

14. The device of claim 13, having an applicator (22) for automatically adding a predefined amount of an activator to the PRP (17), wherein the control module (19) is designed to drive the device such that the following steps are carried out:
   c) adding a predefined amount of an activator to the PRP of the blood sample to be examined after performing the measurement according to step a;
   d) repeating the measurement according to step a after adding the activator to the PRP of the blood sample to be examined and before introducing an aggregation triggered by the activator;
   e) incorporating the measurement results obtained by step d into the determination of step b.

* * * * *